United States Patent [19]

Siehl et al.

[11] Patent Number: 5,780,254

[45] Date of Patent: Jul. 14, 1998

[54] METHOD FOR DETECTION OF HERBICIDES

[75] Inventors: Daniel L. Siehl, Menlo Park; Venkiteswaran Subramanian, Danville; Anne G. Toschi, Burlingame, all of Calif.

[73] Assignee: Sandoz Ltd, Basel, Switzerland

[21] Appl. No.: 767,363

[22] Filed: Dec. 18, 1996

Related U.S. Application Data

[63] Continuation of Ser. No. 508,999, Jul. 28, 1995, abandoned, which is a continuation-in-part of Ser. No. 435,948, May 4, 1995, abandoned.

[51] Int. Cl.[6] .................. C12Q 1/48; C12Q 1/34; C12Q 1/32; C12Q 1/00
[52] U.S. Cl. .................. 435/15; 435/18; 435/2.6; 435/23; 435/4; 536/23.6; 536/23.2; 536/24.3; 536/26.11; 536/26.12; 536/26.13
[58] Field of Search .................. 435/15, 18, 26, 435/23, 4; 536/23.6, 23.2, 24.3, 26.11, 26.12, 26.13

[56] References Cited

U.S. PATENT DOCUMENTS 4,400,529  8/1983  Chin .
4,433,999  2/1984  Hyzak ........................ 71/103
4,645,527  2/1987  Amuti et al. ................ 71/103
4,802,912  2/1989  Baker ......................... 71/103

OTHER PUBLICATIONS

Heim et al; Pesticide Biochem & Physiol; vol. 53, pp. 138–145 (1995).

Hatch, M.D., Phytochem., vol. 6., pp. 115 to 119, (1967).

Haworth et al, J. Agric. Food Chem., vol. 38, pp. 1271–1273 (1990).

Nishimura et al, Phytochem., vol. 34, pp. 613–615 (1993).

*Primary Examiner*—Louise N. Leary
*Attorney, Agent, or Firm*—Lynn Marcus-Wyner; Michael P. Morris

[57] ABSTRACT

This invention relates to novel screening methods for identifying compounds that specifically inhibit a metabolic target site or pathway in plants. Enzymes which are specifically affected by the novel screening method include plant purine biosynthetic pathway enzymes and particularly the enzymes involved in the conversion of IMP to AMP and the conversion of IMP to GMP. Further the invention relates to a method for screening and identifying potential novel compounds that function by the same mode of action as hydantocidin, and the compositions and method of use comprising said compounds.

23 Claims, 9 Drawing Sheets

Retention time, min

1

METHOD FOR DETECTION OF HERBICIDES

This is a continuation application of application Ser. No. 08/508,999, filed on Jul. 28, 1995, abandoned, which is a continuation-in-part application of application Ser. No. 08/435,948, filed on May 4, 1995, abandoned.

BACKGROUND OF THE INVENTION

Hydantocidin and certain hydantocidin derivatives and their use as herbicides are known and described in various references. Hydantocidin is a natural product originally isolated from *Streptomyces hygroscopicus*. Early symptomology of hydantocidin activity in greenhouse tests resembles glyphosate and glufosinate. However, glutamine synthetase is not inhibited by hydantocidin, and growth inhibition due to hydantocidin is not reversed by aromatic amino acids indicating that the mode of action of hydantocidin is different than the mode of action of glyphosate or glufosinate.

We have discovered that the herbicidal activity of hydantocidin and at least some of its derivatives is a result of their inhibition of de novo AMP biosynthesis in the plant purine biosynthetic pathway and specifically is the result of inhibition of the enzyme adenylosuccinate synthetase (ADSS). The discovery of this mode of action along with the screening method used to identify potential inhibitors of the enzymes in the purine biosynthetic pathway is a very advantageous discovery for herbicide development. Typically a chemical is determined to be herbicidal by spraying the chemical on a whole plant or plant part or applying the chemical to the soil prior to seedling emergence. Chemical effect is determined at a specific time interval after chemical application. This process is extremely time consuming and costly. The discovery of the mode of action of hydantocidin and the use of the screening method disclosed herein provides a rapid means for assessing potential herbicidal compounds acting on ADSS or other enzymes in the plant purine biosynthetic pathway.

SUMMARY OF THE INVENTION

This invention relates to novel methods for screening and identifying compounds that specifically inhibit a metabolic target site or pathway in plants. Enzymes which are specifically targeted by the novel screening method include plant purine biosynthetic pathway enzymes and particularly enzymes that inhibit AMP and GMP biosynthesis.

Therefore, one of the main objectives of the invention was to develop a screening assay for identifying inhibitory compounds of the plant purine biosynthetic pathway that could potentially act as herbicides.

Accordingly, the present invention comprises a method of identifying potential inhibitors of the plant purine biosynthetic pathway which are potential herbicides and further comprises testing an inhibitor thus identified, also referred to as a probe compound, in a lethal concentration and reversal assay. This two-step procedure includes determining the lethal concentration of the probe compound and reversion of the inhibition at the lethal concentration of the probe compound in the presence of antidote compounds described hereinbelow. The invention further relates specifically to novel compounds which inhibit IMP, AMP and GMP biosynthesis, and specifically the target enzyme adenylosuccinate synthetase (ADSS) either found by the methods described herein or as determined by other methods.

In another aspect, the invention includes an in vitro enzyme assay with the enzymes of the purine biosynthetic pathway to confirm inhibition by a probe compound. The assay described herein may be used to screen for plant purine biosynthetic pathway inhibitors overall. More specifically the in vitro assay may be used to determine that the mode of action of a probe compound is the same as the mode of action of hydantocidin and 5'-Phospho-N-acetyl-hydantocidin (NAP-H).

Another aspect of the present invention is a method for the control of undesirable plant growth which comprises applying to a locus where control is desired a herbicidally effective amount of an inhibitory compound identified according to the methods disclosed herein.

According to still another aspect the invention is a herbicidal composition comprising an inhibitor compound of the invention as an active ingredient in combination with an agriculturally acceptable carrier.

DETAILED DESCRIPTION OF THE INVENTION

To assist in interpreting the means and scope of the present invention, the following terms and abbreviations are intended to have the meaning described herein:

ADSS=adenylosuccinate synthetase.
AMP=adenosine monophosphate
ADP=adenosine diphosphate
AICAR=5-aminoimidazole-4-carboxamide ribotide
AICARP=5-aminoimidazole-4-carboxamide ribotide 5' phosphate
AIR=aminoimidazole-4-carboxamide-1-b-D-ribofuranosyl-5-monophosphate
AS=adenylosuccinate
ASL=adenylosuccinate lyase
ATP=adenosine triphosphate
FAD=flavin adenine dinucleotide
GAR=glycinamide ribotide
GA=glycinamide
GDP=guanosine diphosphate
GMP=guanosine monophosphate
GTP=guanosine triphosphate
HPLC=high pressure liquid chromatography
IMP=inosine monophosphate
XMP=xanthosine monophosphate
NAP-H=5'-Phospho-N-acetyl-hydantocidin also known as N-acetylphospho-hydantocidin PRPP=phosphoribosyl pyrophosphate
R5P=ribose-5-phosphate
EDTA=ethylene diamine tetraacetic acid—disodium salt
DTT=dithiothreitol
EPPS=N-(2-Hydroxyethyl)piperazine-N'-(3-propanesufonic acid).

Figure 1A:
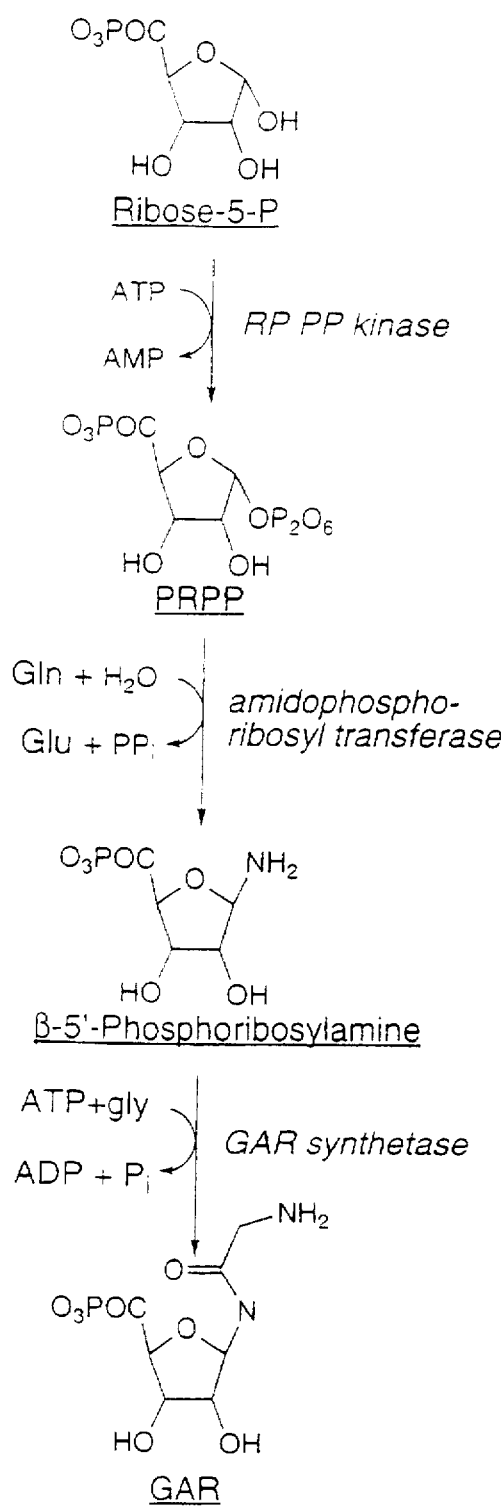
FIG. 1 depicts the IMP biosynthetic pathway.
Figure 1B:
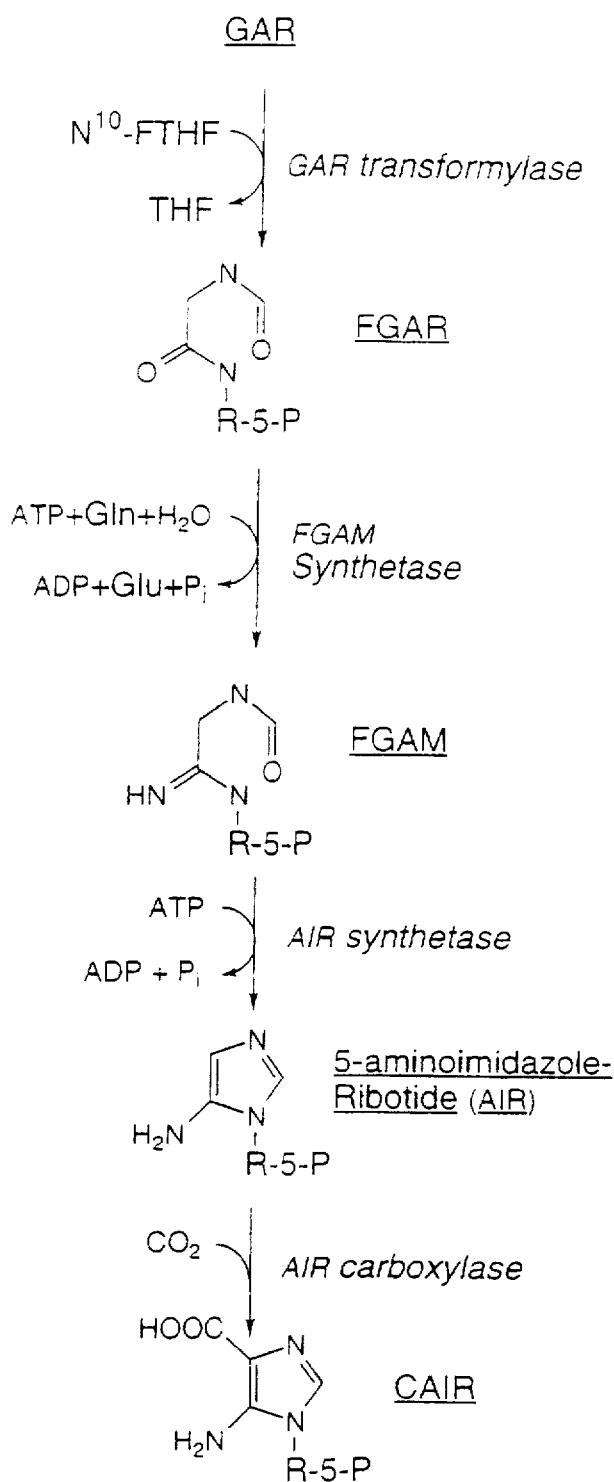
Figure 1C:
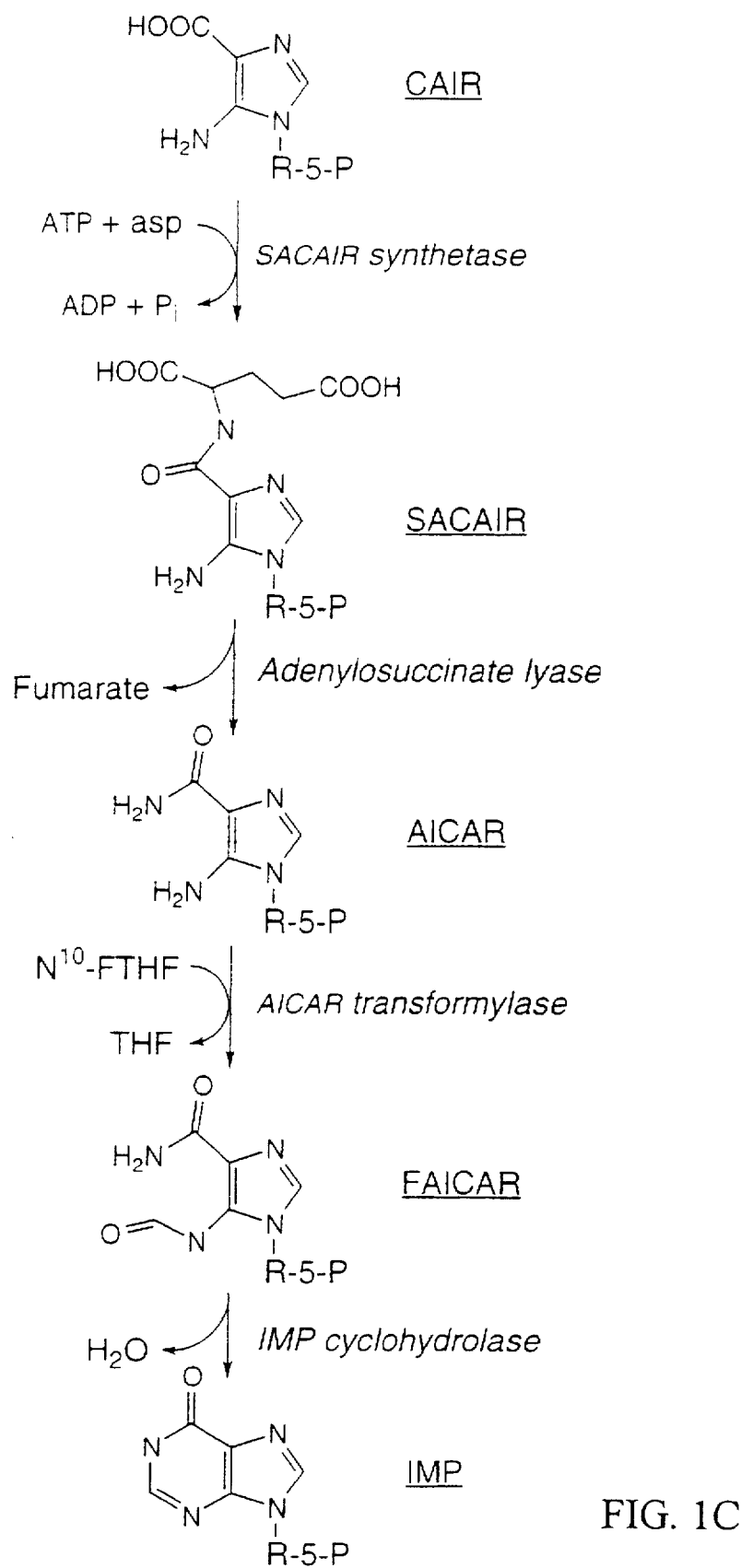
Figure 2:
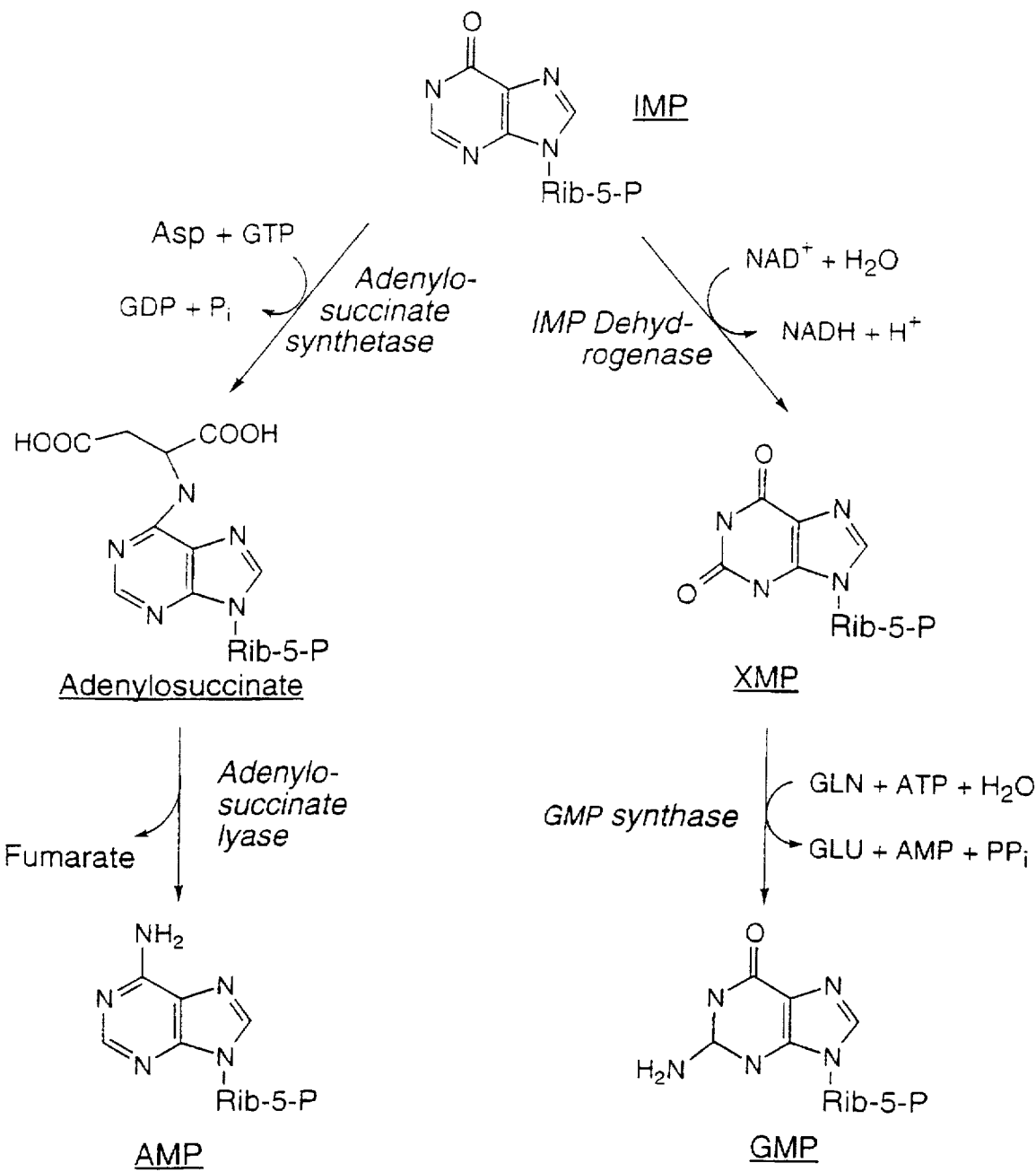
FIG. 2 depicts the pathway for the conversion of IMP to AMP and GMP.

An "enzyme inhibitory effective amount" means an amount of a probe compound which causes a significant decrease in the ability of a plant purine biosynthetic pathway enzyme to convert substrate into product as measured by quantified enzymatic activity as generally known to those skilled in the art. The preferred measurement being made by spectrophotometric assays. A significant decrease is preferably a decrease of at least 50%, more preferably is a decrease of at least 90% and most preferably is a decrease of at least 95% as compared to the amount of product produced under the same conditions without the probe compound. The plant purine biosynthetic pathway is illustrated in FIGS. 1 and 2 and includes the conversion of R5P to AMP or GMP.

The term "IMP biosynthesis" means the conversion of R5P into IMP. "AMP biosynthesis" means the conversion of IMP into AMP. The term "GMP biosynthesis" means the conversion of IMP into GMP. Specifically the term "AMP biosynthetic inhibitory effective amount" means an amount of a probe compound which causes a significant decrease in the ability of ADSS or ASL to convert the substrate, IMP into product AMP in the presence of GTP and aspartate as measured by quantified enzymatic activity as generally known to those skilled in the art. The term "GMP biosynthetic inhibitory effective amount" means an amount of a probe compound which causes a significant decrease in the ability of IMP dehydrogenase or GMP synthase to convert the substrate, IMP into product GMP in the presence of NAD, ATP and glutamine as measured by quantified enzymatic activity as generally known to those skilled in the art. The same definition is applied to any plant purine biosynthetic pathway enzyme which is inhibited by a probe compound, for example, IMP dehydrogenase inhibitory effective amount, GMP synthase inhibitory effective amount and the like. However, the substrates and products will obviously differ.

A "probe compound" is a compound used in the methods described herein which potentially inhibits directly or indirectly one or more of the plant purine biosynthetic pathway enzymes. Unless indicated otherwise, the term "plant purine biosynthetic pathway enzyme" as used herein refers to any enzyme which is involved in the purine biosynthetic pathway as depicted in FIGS. 1 and 2 and includes PRPP kinase, amidophosphoribosyl transferase, GAR synthetase, GAR transformylase, FGAM synthetase, AIR synthetase, AIR carboxylase, SACAIR synthetase, adenylosuccinate lyase, AICAR transformylase, IMP cyclohydrolase, IMP dehydrogenase, GMP synthase, adenylosuccinate synthase and adenylosuccinate lyase. A plant purine biosynthetic pathway inhibitor is an inhibitor or probe compound that inhibits any of plant purine biosynthetic pathway enzymes.

Compounds which are particularly preferred are those probe compounds which inhibit GMP biosynthesis and AMP biosynthesis. Particularly preferred target enzymes are ADSS, ASL, IMP. dehydrogenase and GMP synthase. The most preferred target enzyme is ADSS. The screening methods described herein provide an efficient and rapid way for determining the herbicidal potential of probe compounds. Compounds identified by the methods described herein may be used as herbicides or proherbicides to inhibit plant growth.

Lethal concentration is the concentration of a probe compound which causes about 80% or greater growth inhibition when compared to a control, and more preferably causes about 90% or greater growth inhibition. LC 90 is the concentration used to cause 90% growth inhibition of the plants as compared to control plants. One skilled in the art will recognize that the term LD 90 is also used in this context. No growth would be equal to 100% growth inhibition.

The term "plant material" includes seed; seedlings; parts of young plants, such as meristematic tissue, leaf tissue, root tissue, and shoot tissue; callus and other cultures. Preferred plant materials of the screening method of the present invention are seeds, particularly Arabidopsis seed and grass seed such as bent grass.

The terms "herbicide" and "herbicidal" used herein denote the inhibitive control or modification of undesired plant growth. Inhibitive control or modification includes all deviation from natural development such as for example, total killing, growth retardation, defoliation, desiccation, stunting, tillering, stimulation, leaf burn and dwarfing. The term "herbicidally effective amount" denotes any amount which achieves such control or modification when applied to undesired plants themselves or to a locus where control is desired. The term "plant" is intended to include germinant seed, emerging seedlings and established vegetation including roots and above ground portions.

Test conditions suitable for growth are those conditions wherein the control plant material used in the screen, described herein, will grow normally. These conditions are easily determined by one skilled in the art. Reversal conditions are those conditions in which inhibition which occurs at the lethal concentration is reversed as determined by exposure of the plant material to combinations of the probe compound and to one or more antidote compounds. The recovery of growth is about at least 50% or more. An antidote compound is a compound that causes reversal of inhibition of a probe compound. As an example, with respect to inhibitors of ADSS, antidote compounds would include AMP, ADP, adenosine and adenine. The antidote compounds for ASL would also include adenine, AMP, adenosine and ADP; the antidote compounds for GMP synthase would include GMP, guanine and guanosine and the antidote compounds for IMP dehydrogenase would include XMP, GMP, guanine and guanosine.

This invention further relates to the mode of action of hydantocidin and certain hydantocidin derivatives which are not claimed in the present invention. Hydantocidin and N-acetyl hydantocidin are known herbicidal compounds, however the mode of action of said compounds and their derivatives was previously unknown. We have discovered that hydantocidin and N-acetyl hydantocidin are inhibitors of purine biosynthesis and specifically inhibit AMP biosynthesis defined herein as the conversion of inosine monophosphate (IMP) to adenosine monophosphate (AMP). The biochemical pathway and conversion of IMP to AMP is depicted in FIG. 2. Two enzymes are involved in the conversion of IMP to AMP. The first enzyme is ADSS which catalyzes the conversion of IMP to adenylosuccinate (AS). The second enzyme adenylosuccinate lyase (ASL) catalyzes the conversion of AS to AMP.

When the in vitro assay described herein is used with the enzymes ADSS and ASL and the compounds N-acetylphosphohydantocidin (NAP-H) and hadacidin, it has been determined that each compound is an inhibitor of ADSS. ASL is not inhibited by said compounds. However, hydantocidin and N-acetyl hydantocidin must be phosphorylated to inhibit ADSS. Since some of the substrates of ADSS such as IMP and GTP are phosphorylated, it is hypothesized that hydantocidin, N-acetyl hydantocidin and derivatives thereof are proherbicides and must be phosphorylated in the 5'-position of the ribose moiety in the plant in order to become an effective inhibitor of ADSS. By the same token, it is contemplated that a probe compound may also require phosphorylation prior to its binding with ADSS. The phosphorylation may be by a nucleotidase, kinase or other means known to those skilled in the art. This means of activation, the phosphorylation of a probe compound is also considered part of the invention.

The dephosphorylation of NAP-H and derivatives, by phosphatase or other means of removing phosphate groups, prior to their contacting ADSS may provide a method of inactivating the inhibitory effects of hydantocidin and its derivatives and this means of inactivation is also considered a part of the invention. In this respect, the invention also contemplates a method of inactivating the AMP biosynthetic inhibitory effect or ADSS inhibitory effect of a probe compound wherein said probe compound inhibits ADSS by the same mode of action as NAP-H, comprising applying to a plant or a locus where control is desired an inhibitory compound which is dephosphorylated prior to contacting ADSS.

Additionally, chemical analogs that mimic phosphorylated derivatives such as phosphonate analogs of hydantocidin and N-acetyl hydantocidin may also be effective inhibitors of ADSS.

Not all inhibitors of ADSS have to be phosphorylated. Hadacidin, a known compound that blocks the conversion of IMP to AMP by a mechanism that is different from NAP-H is an example of an inhibitor of ADSS that is not a phosphorylated compound.

To identify inhibitory compounds, a lethal concentration and reversal assay screen was developed which utilizes Arabidopsis seeds. This assay involves a two-step screening. In the first step, the lethal concentration of a probe compound is determined and reversal of inhibition is determined in the second step. For hydantocidin inhibition at the lethal concentration in the presence of AMP, ADP or adenine is demonstrated to be completely reversed. The % recovery of growth is then determined and is about between 50 and 100%.

The Arabidopsis bioassay results reported in Table 1 indicate that hydantocidin, N-acetyl hydantocidin, NAP-H, and hadacidin are blocking the biosynthesis of AMP from IMP. Based on these results, the mode of action of hydantocidin and NAP-H is confirmed as inhibition of biosynthesis of AMP, due to inhibition of either ADSS or ASL. Subsequent assay of said enzymes confirmed that the enzyme inhibited by NAP-H is ADSS.

In one embodiment, the invention is a method for identifying a probe compound that inhibits AMP biosynthesis, said method comprising;
 a) exposing plant material capable of expressing the enzyme adenylosuccinate synthetase and adenylosuccinate lyase to a concentration range of a probe compound;
 b) determining a lethal concentration range of said probe compound;
 c) exposing plant material capable of expressing said enzyme to the lethal concentration range of said probe compound and concurrently exposing said material to a concentration range of one or more antidote compounds; and
 d) identifying a probe compound that inhibits growth of the plant material at a lethal concentration but does not inhibit growth of the plant material when exposed to the antidote compound.

A further embodiment includes a method for identifying a probe compound that inhibits plant AMP biosynthesis, said method comprising a two-step procedure.
 a) wherein the first step includes the determination of a lethal concentration which comprises:
  1) maintaining plant material capable of expressing the enzyme adenylosuccinate synthetase and adenylosuccinate lyase under test conditions suitable for growth of the plant material;
  2) contacting a probe compound at a concentration range of about 0.01 ppm to about 500 ppm with the plant material of 1);
  3) allowing the probe compound and plant material to incubate; and
  4) measuring the inhibition of growth of the plant material and determining the lethal concentration of the probe compound;
 b) wherein the second step includes the determination of reversal conditions which comprises:
  5) maintaining plant material as stated in step 1);
  6) contacting the plant material with the probe compound and one or more antidote compounds wherein the concentration of the probe compound is at the lethal concentration and the concentration of the antidote compound is in the range of about 0.001 mM to about 5.0 mM;
  7) allowing the plant material to grow in the presence of the probe compound and antidote compound;
  8) measuring the growth of the plant material and
 selecting the probe compound that inhibits growth of the plant material under step a) but does not inhibit growth of the plant material under reversal conditions of step b).

In general, the preferred plant material in the assay is seed material and particularly Arabidopsis seed. However, one skilled in the art could easily use seeds of other plant species. If seed material is used, it is preferable to determine the lethal concentration and the reversal conditions independently after about 5 days, but before 14 days. One skilled in the art would be able to determine the preferred effective concentration range of a probe compound to determine lethal concentration of that particular probe compound by routine experimentation. For example, probe compounds tested in the method should be supplied at a concentration range as described above, about 0.01 ppm to 500 ppm, a preferred range is about 0.05 ppm to about 250 ppm and more preferred concentration range is about 0.1 to about 100 ppm. Concentrations higher than 500 ppm would be similarly effective but may be wasteful and are usually not necessary. A preferred concentration range of the antidote compound is about 0.001 mM to about 5.0 mM and more preferably about 0.005 mM to 1.0 mM.

While it is preferred to determine the lethal concentration at a LC 90 value, values less than 90% can be used, for example 80%. As can be appreciated, the antidote compound will vary depending on the target enzyme. With ADSS, the preferred antidote compounds include ADP, AMP and adenine.

Further, the method described herein can be used to discover inhibitors that block any of the fifteen enzymes in the purine biosynthetic pathway depicted in FIGS. 1 and 2. These enzymes are collectively referred to as plant purine biosynthetic pathway enzymes. The method for screening and identifying a compound that inhibits plant purine biosynthetic pathway enzymes comprises a two step procedure,
 a) the first step includes the determination of a lethal concentration which comprises:

1) maintaining plant material capable of expressing a plant purine biosynthetic pathway enzyme under test conditions suitable for growth of the plant material;
2) contacting a probe compound at a concentration range of about 0.01 ppm to 500 ppm with the plant material of 1);
3) allowing the probe compound and plant material to incubate; and
4) measuring the inhibition of growth of the plant material and determining the lethal concentration of the probe compound;

b) the second step includes the determination of reversal conditions which comprises:
5) maintaining plant material as stated in step 1);
6) contacting the plant material with the probe compound and one or more antidote compounds wherein the concentration of the probe compound is at the lethal concentration and the concentration of the antidote compounds are in the range of about 0.001 mM to about 5.0 mM;
7) allowing the plant material to grow in the presence of the probe compound and antidote compound;
8) measuring the growth of plant material and identifying a compound that inhibits growth of the plant material under test conditions but does not inhibit growth of the plant material under reversal conditions.

Another preferred embodiment of the invention includes a method for identifying a probe compound that inhibits plant AMP biosynthesis, said method comprising a two step procedure, a) wherein the first step includes the determination of a lethal concentration which comprises:
1) adding a concentration range of about 0.01 to about 500 ppm of a probe compound to wells of a support;
2) dispensing media capable of sustaining growth in said wells;
3) adding plant seeds capable of expressing the enzyme adenylosuccinate synthetase or adenylosuccinate lyase to the media to said wells;
4) allowing the probe compound and the seeds to incubate under test conditions suitable for growth of said seed;
5) measuring the inhibition of growth of the seeds; and
6) determining the lethal concentration of the probe compound; and b) wherein the second step includes the determination of reversal conditions which comprises:
7) adding about the lethal concentration of the probe compound to wells in a support;
8) adding one or more antidote compounds separately to said wells;
9) dispensing media capable of sustaining growth in said wells
10) adding plant seeds capable of expressing the enzyme adenylosuccinate synthetase or adenylosuccinate lyase to the media in said wells
11) allowing the seeds to germinate in the presence of the probe compound and antidote compound;
12) measuring the growth of said seeds as compared to a control wherein the control lacks the antidote compound of step 8) and identifying a compound that inhibits growth of the seeds under the lethal concentration but does not inhibit growth of said seeds under reversal conditions.

In another preferred embodiment, the invention includes the above described two-step method for identifying a probe compound that inhibits GMP biosynthesis, however, the enzymes that are inhibited would include IMP dehydrogenase or GMP synthase. Additionally, the disclosed method can be used to identify a probe compound that inhibits IMP biosynthesis.

The media used for seedling growth may be any media suitable for maintaining plant growth and preferably contains macro and micronutrients which are supplemented with a sugar source, preferably sucrose. In a preferred embodiment, the media will be a mixture of the above components and agar which is then dispensed into wells. There are numerous commercially available sources of agar and some examples include Sigma Bacteriological Agar and Phytagar. However, one skilled in the art will appreciate that any type of gelatin material could be suitable.

While the term "well or wells" is used to indicate the space in which the media and plant material are placed, synonymous terms are equally applicable, and include for example, openings, pores, slots, spaces and the like. A support can be any container or material that will hold the media and plant material to provide an environment for plant growth, while tissue culture cell wells are preferred other examples include, pill bottles, petri plates and the like.

Plant growth can be measured by means known to those skilled in the art and include measurements of root growth, leaf growth, inhibition and leaf malformation. In the preferred embodiment seedling growth is measure by scoring shoot, leaf and root growth relative to a control.

Specifically with regard to the inhibition of AMP biosynthesis, once a probe compound is screened and identified by the two step lethal concentration and reversal assay described above, a further in vitro enzyme assay may be used to confirm that said probe compound acts by the same mode of action as hydantocidin. Additionally the in vitro enzyme assay may be used independently of the two-step assay.

In this regard, the invention further includes a method for determining the mode of action of a probe compound using an in vitro enzyme assay comprising;

a) obtaining substantially pure ADSS;
b) mixing the probe compound with ADSS, GTP and aspartate;
c) allowing pre-incubation of the reaction mixture;
d) adding substrate IMP and allowing the substrate and reaction mixture to react;
e) monitoring the formation of AS as influenced by the probe compound; and
f) comparing the amount of AS produced in the presence of the probe compound with that produced with the absence of the probe compound.

In addition to the specific ADSS source described in the Examples, ADSS may be obtained from a number of sources, including but not limited to wheat germ, enteric bacteria and mammalian liver or muscle. The ADSS must be substantially pure, which means that it must be free of nucleotidase activity which would remove the phosphate group from IMP, and free of unwanted GTPase activity which would generate excessive GDP, a known inhibitor of the reaction. When these requirements are not met, degradation of IMP and GTP may occur, the primary consequence of which is complete inhibition of the reaction before sufficient AS has been generated to accurately quantify the extent of the reaction. Sufficient purification of ADSS from maize seedlings is obtained by the combination of ammonium sulfate fractionation, DEAE-cellulose chromatography and gel filtration chromatography, or ammonium sulfate fractionation and hydrophobic interaction chromatography. These techniques are well known to those skilled in the art. An HPLC anion exchange column is the preferred instrumentation used for monitoring AS formation.

The concentration range of ADSS in the assay is preferably sufficient to generate a range of 10 µM to 50 µM AS during the time span of about 60 minutes. The concentration range of a probe compound depends on the specific compound but should be in the range of about 0.5 to about 150 µM, and preferably about 1.0 to about 100 µM. The concentration ranges of GTP, aspartate and IMP present at the start of the reaction are preferably about 70–200 µM, 3–10 mM and 100–400 µM, respectively.

Optionally phosphate can be added to the reaction mixture to speed the reaction. The pre-incubation period can vary but is preferably about 10 minutes. Phosphate is necessary to observe inhibition by NAP-H.

Alternatively, the mode of action of a probe compound may be determined by the following spectrophotometric method which comprises:

a) obtaining substantially pure ADSS;

b) mixing the probe compound with ADSS, GTP and aspartate;

c) allowing pre-incubation of the reaction mixture;

d) adding a substrate IMP and allowing the substrate and reaction mixture to react; and e) measuring the formation of product AS.

More specifically the formation of AS is monitored by measuring the increase in optical density at 280 nm. The spectrophotometric procedure is preferably used only after establishing that the preparation of ADSS meets the criteria for "substantially pure" as defined above. This is preferably achieved by use of the HPLC assay, which enables one to observe degradation of the substrates, and to quantify the stoichiometric relationship between formation of AS and GDP, which should be about 1 to 1. Furthermore, the HPLC procedure serves as a backup in cases where the probe compound causes interference in the spectrophotometric assay. Such interference may comprise excessive absorbance at 280 nm, or degradation of the probe compound by enzymes present in the ADSS preparation. When a probe compound causes absorbance outside of the linear range of the spectrophotometer at the outset of the reaction, one skilled in the art can use the HPLC assay.

ADSS negative control reactions wherein a probe compound is not present, proceed linearly with time until about 8 to 12%, and preferably 10% of the GTP has been converted to GDP. At this time the reaction rate becomes measurably slower. Eventually there is no further net formation of AS. The final concentration of AS attained can be increased by providing a larger signal for the detector, by optionally including a system for regenerating GTP in the reaction mixture. The system comprises phosphoenolpyruvate at a concentration of about 0.3 to 2.0 mM, preferably of about 0.5 to 1.0 mM, and the enzyme pyruvate kinase at a concentration sufficient to catalyze the reaction of phosphoenolpyruvate with GDP at a rate faster than the rate of ADSS reaction. Pyruvate kinase from various organisms is commercially available.

The in vitro enzyme assay developed herein can be used to screen and identify new inhibitors of plant ADSS. These compounds may be analogs of plant specific products based on existing chemistry or naturally occurring inhibitors of plant ADSS.

One skilled in the art will appreciate that the assay system described herein may be modified in various aspects without changing the essence of the invention. Additionally, one skilled in the art can readily substitute functionally equivalent test methods.

The probe compounds that have been identified according to the invention as inhibiting the plant purine biosynthetic pathway as well as other hydantocidin compounds can be further evaluated by testing the compound on whole plants in typical herbicidal greenhouse tests well known to those skilled in the art.

The purine biosynthetic inhibitors according to the invention, particularly the AMP or GMP biosynthesis inhibitors of the enzymes ADSS, ASL, IMP dehydrogenase and GMP synthase may be employed in herbicidal compositions, and these compositions form an important embodiment of the present invention. The purine biosynthetic inhibitor comprises the active ingredient of the composition generally with an inert ingredient. The compositions may be formulated as either concentrated formulations or as dust or granular formulations. The formulations are prepared according to procedures which are conventional in the agricultural arts. In general the formulations may include 0.01 to 99% by weight of active ingredient, 0 to 40% by weight of agriculturally acceptable surfactant and from 0.1 to 99.99% of solid or liquid diluent(s). The active ingredient consists of at least one compound of the invention or mixtures thereof with other active ingredients. Surfactants are agriculturally acceptable materials which impart emulsifying, spreading, wetting, dispersibility or other surface-modifying properties to formulations. A diluent is any liquid or solid agriculturally acceptable material which may be added to the active constituent to bring it in an easier or improved form.

Further the inhibitory compounds of the present invention may be used to control undesired plant growth and may be used for the control of both broad leaf and grassy weeds in preplant incorporation and pre- and post-emergent application. Inhibitory compounds may also exhibit selectivity in various crops and thus be suited for use in weed control in crops such as but not limited to corn, cotton, wheat, soybean, rice, sugarbeet and sunflower.

The following non-limiting examples are provided to illustrate the invention further.

EXAMPLE 1

Determination of the Lethal Concentration of the Test (Probe) Compounds

Figure 3:
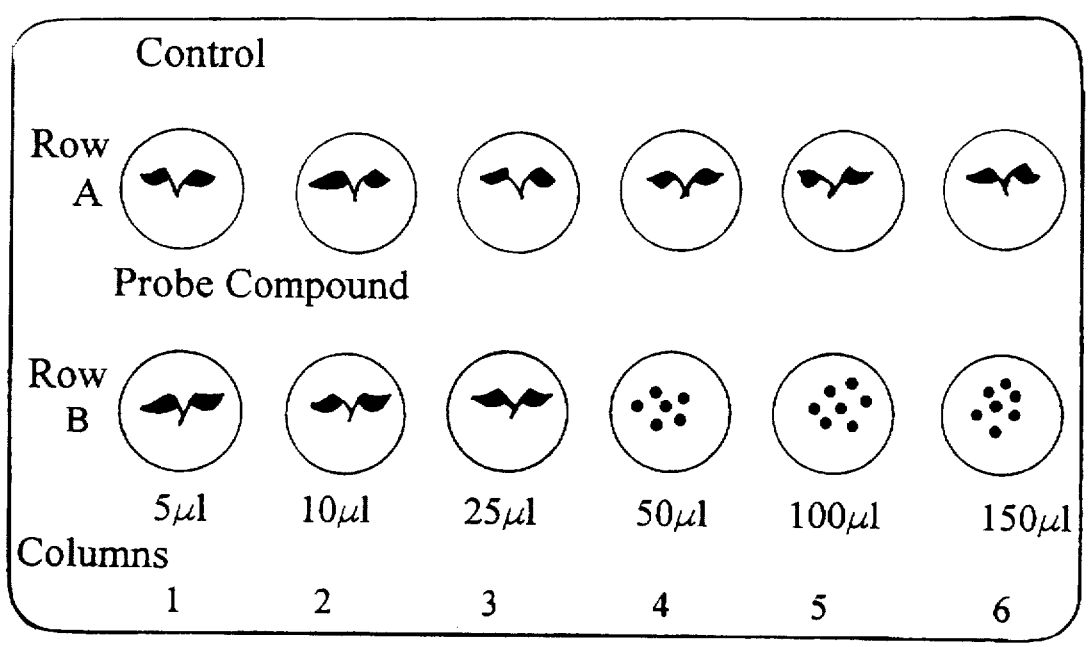
FIG. 3 illustrates schematically the lethal concentration step of the claimed assay procedure. Row A is the control row and does not contain a probe compound. Row B contains 6 concentrations or doses of an aqueous solution of the probe compound.

Stock solutions of probe compounds are made at 500 ppm in distilled water or a suitable solvent that does not affect plant growth. Arabidopsis bioassays are conducted in 24-well sterile microtiter plates. In a typical microtiter plate, there are 4 rows of 6 wells each. Row A consisting of 6 wells is designed for control with no test compounds. Rows B, C and D are designated for various probe compounds. Probe compounds are added into the wells in appropriate volumes in mL. Each row of six wells represents a concentration range of 0.1 to 150 ppm. (FIG. 3 illustrates the use of a 12-well microtiter plate.)

Each microtiter plate requires 40 ml of Arabidopsis seed media. The seed media consists of 5 ml MS micronutrient 100× concentrated solution and 50 ml MS macronutrient 10× concentrated solution supplemented with 1% w/v of sucrose and brought to 1.0 liter with water. The media is adjusted to pH 6.6. Phytagar is added to the media for a final concentration of 0.7% w/v. The media is autoclaved under standard conditions for 20 minutes. After cooling the media to about 45° C., 1.0 ml of the media is dispensed in each well of the microtiter plate.

About 100 mg of Arabidopsis seeds are sterilized by rinsing thoroughly in 50 ml of 20% bleach containing 2.0 mL/ml of 20% Triton X100. Typically this is done with 45 ml of sterilant in a 50 ml sterile tube. After shaking the seeds for 10 minutes, the seeds are allowed to settle under gravity, the sterilant is removed and the seeds are rinsed six times with sterile water. After the final rinse, all but approximately 3.0 ml of the water is removed. The sterile seeds can be stored at 4° C. for approximately 3 weeks and used repeatedly. Between 10–20 seeds are dispensed in each well using a 1.0 ml pipette. The microtiter plate is then closed, taped and incubated at about 28° C. for 7 days. Growth is scored visually, as a % of control. 100% growth inhibition is equivalent to no growth, for example seeds only; 95% growth inhibition is equivalent to 5% growth, for example only root growth and small leaf growth; and 90% growth inhibition is equivalent to 10% growth, for example about 1/10 of the control growth. Concentration of the compound causing 90% or greater growth inhibition (LC 90) compared to controls is designated as lethal concentration. Results of a typical assay are shown in FIG. 3. Using this procedure, lethal concentrations of hydantocidin, N-acetyl hydantocidin, N-acetylphospho-hydantocidin and hadacidin were determined as approximately 2.0, 12.0, 8.0 and 50 µM respectively. The calculation for lethal dose is as follows:

a. $\dfrac{(\mu l \text{ of lowest dose showing 90\% growth inhibition})(\text{ppm tested})}{1000} = \text{ppm in well}$ b. $\dfrac{(\text{ppm in well})(1000)}{\text{mw of the compound}} = \mu M \text{ of compound in the well}$

EXAMPLE 2

Identification of AMP Biosynthesis Inhibitors

Figure 4:
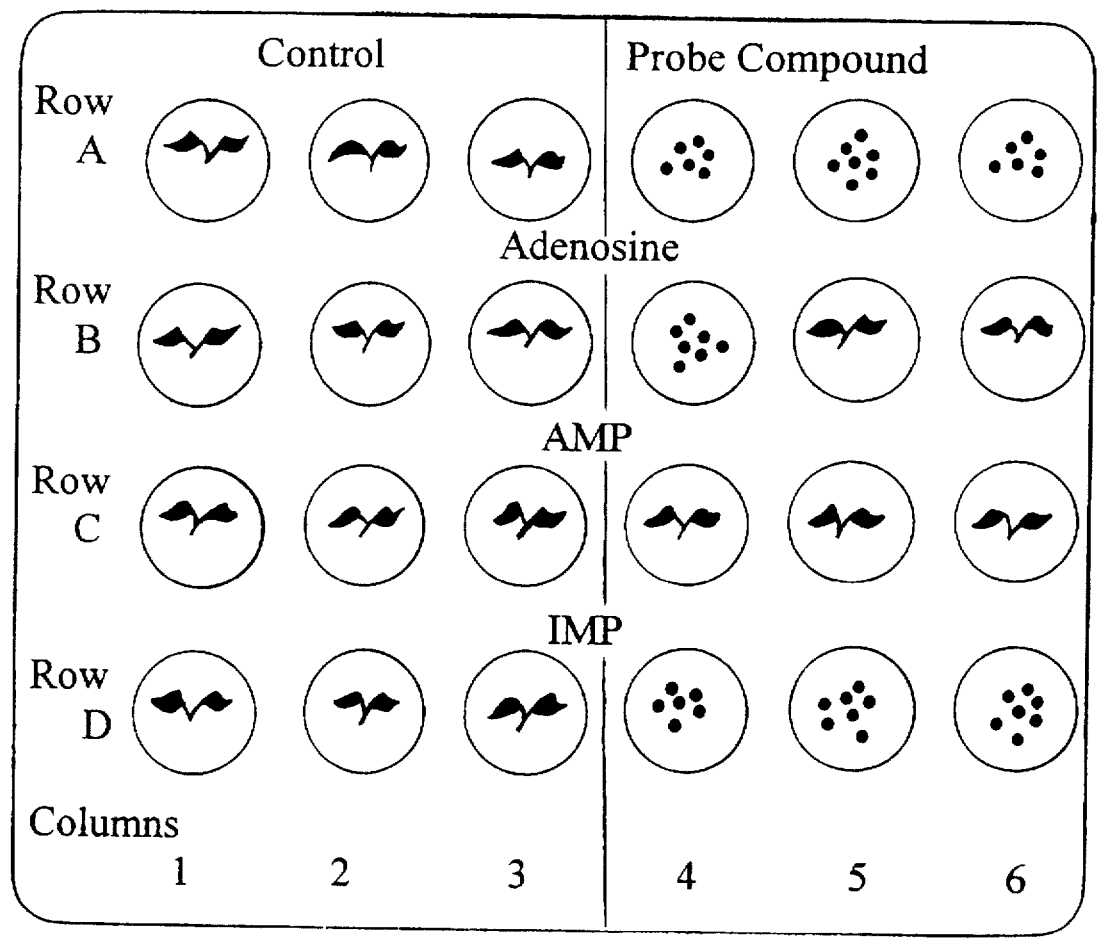
FIG. 4 illustrates schematically the reversal step of the claimed assay procedure.

Stock solutions (0.5% w/v) of antidote compounds; ADP, IMP and adenine are prepared at 2% w/v (except where indicated). The solutions are filter sterilized prior to addition. FIG. 4 represents a typical set up in a reversion assay for discovering inhibitors of AMP biosynthesis.

The left side (columns 1–3) of the 24-well microtiter plate is designed for controls, and the right side (columns 4–6) are designated for one probe compound. The first row (A) does not have added antidote and is used as a check. Rows B,C and D are supplemented with three doses of an antidote for the control and probe compound. In the example shown in FIG. 4, the antidotes used are adenosine, AMP and IMP. The three doses are 50,100 and 150 µl respectively.

Forty ml of Arabidopsis growth media as described in Example 1 is sterilized and allowed to cool to about 45° C. A probe compound (at 1.5× lethal concentration) is added to columns 4 through 6 (right half of the plate). Media is distributed at 1.0 ml per well to all wells. Sterile seeds are added to each well as described above. As in Example 1, the plate is incubated and growth is scored.

Using this procedure for hydantocidin, it is determined that growth occurred in all wells in columns 1 through 3. This result indicates that the selected antidote compounds, IMP, adenosine and AMP have no effect on the growth of the plant. Growth is not observed in the top row, wells 4 through 6 due to the lethal effects of the probe compound. Also IMP did not reverse growth inhibition and therefore is not an antidote for this particular test. Complete growth is observed in rows B and C, wells 4 through 6, indicating that adenosine and AMP are able to reverse the growth inhibition. Lack of growth in well (row B, column 4) may be due to insufficient adenosine to reverse growth inhibition.

The above two-step process is conducted with hydantocidin, (Hyd); N-acetyl hydantocidin, (NA-H); NAP-H and hadacidin, (Had), in the presence of various antidotes and the results are shown in Table 1 below. All four compounds specifically block the conversion of IMP to AMP.

TABLE 1

Effect of Various Antidotes on Arabidopsis Inhibition by Compounds Listed

| Antidote Added to Standard Arabidopsis Growth Media | Concentration (mM) | Growth, % of Control | | | |
|---|---|---|---|---|---|
| | | Hyd | NA-H | NAP-H | Had |
| No antidote | 0 | 0 | 0 | 0 | 0 |
| Adenine | 0.5–5.0 | 60 | 60 | 65 | 55 |
| Adenosine | " | 80–100 | 80–100 | 80–100 | 80–100 |
| Guanine | " | 0 | 0 | 0 | 0 |
| Guanosine | " | 0 | 0 | 0 | 0 |
| Adenosine + Guanosine | " | 80 | 80 | 80 | 80 |
| Cytidine + Uridine | " | 0 | 0 | 0 | 0 |
| AMP | " | 100 | 100 | 100 | 100 |
| ADP | " | 100 | 100 | 100 | 100 |
| ATP | " | 40 | 40 | 40 | 40 |
| IMP | " | 5 | 5 | 5 | 5 |
| Hypoxanthine | " | 0 | 0 | 0 | 0 |

Growth is not observed in the presence of Hyd, NA-H, NAP-H or Had without the antidote, and 0 is equal to no growth.

EXAMPLE 3

Identification of GMP Biosynthesis Inhibitors

The two-step process described in Examples 1 and 2 above is conducted in the same manner with Mycophenolic Acid (MPA) in the presence of various antidotes and the results are shown in Table 2 below. MPA is a known inhibitor of IMP to GMP conversion. The lethal concentration is determined to be 12.5 ppm.

TABLE 2

Effect of Various Antidotes on Arabidopsis Inhibition by MPA

| Antidote Added to Standard Arabidopsis Growth Media | Concentration (mM) | Growth, % of Control |
|---|---|---|
| No antidote | 0 | 0 |
| Adenine | 0.5–5.0 | 0 |
| Adenosine | " | 5 |
| Guanine | " | 40 |
| Guanosine | " | 80 |
| AMP | " | 5 |
| GMP | " | 90 |
| IMP | " | 5 |

Growth is not observed in the presence of MPA without the antidote, and 0 is equal to no growth.

EXAMPLE 4

Identification of IMP Biosynthesis Inhibitors

The two-step process described in Examples 1 and 2 above is conducted in the same manner with 1,2,4-triazole- 3-carboxamide-1-ribose (TCR) in the presence of various antidotes and the results are shown in Table 3 below. The lethal concentration is determined to be 200 ppm.

TABLE 3

Effect of Various Antidotes on Arabidopsis Inhibition by TCR

| Antidote Added to Standard Arabidopsis Growth Media | Concentration (mM) | Growth, % of Control |
|---|---|---|
| No antidote | 0 | 0 |
| AMP | 0.5–5.0 | 70 |
| IMP | " | 70 |
| GMP | " | 80 |

Growth is not observed in the presence of TCR without the antidote, and 0 is equal to no growth.

EXAMPLE 5

Enzyme Assays

Based on the Arabidopsis bioassay results disclosed in Table 1, it is concluded that hydantocidin, N-acetyl hydantocidin, N-acetylphosphohydantocidin and hadacidin inhibit either ADSS or ASL. ADSS and ASL are isolated from maize seedlings and assayed for inhibition.

A. Preparation of ADSS:

ADSS is obtained from 4–5 day old, etiolated seedlings of *Zea mays*. Seedlings are homogenized in a Waring blender with an equal volume (grams of tissue=mls of buffer) of extraction buffer containing 50 mM EPPS, pH 7.5, 5 mM $MgCl_2$, 0.1 mM EDTA, 5 mM sodium bisulfite, 5 mM DTT, 0.1 mM phenylmethanesulfonyl fluoride and 10% glycerol. The extract is expressed through Miracloth (Calbiochem, La Jolla, Calif.) sandwiched between layers of cheesecloth. To precipitate phenolics and nucleic acids, 0.2 to 0.4% w/v protamine sulfate is added to the extract. The extract is stirred for 30 minutes, and then centrifuged at 45,000×G for 60 minutes. The resulting supernatant is fractionated with ammonium sulfate. Proteins are retained which precipitate at concentrations of ammonium sulfate greater than 45% saturation, but less than 55% saturation. Similar methods are used to isolate ADSS from wheat germ, *E. coli* and rat liver. ADSS activity is further purified by subjecting the preparation to DEAE cellulose chromatography. The column is equilibrated with chromatography buffer consisting of 50 mM EPPS, pH 7.5, 10% glycerol, 0.1 mM EDTA, 5 mM $MgCl_2$ and 1 mM DTT. After loading the enzyme preparation, the column is washed with two bed volumes of the chromatography buffer, then eluted with a linear, 10-bed-volume gradient of 0 to 0.4M KCl dissolved in the same buffer. The peak of ADSS activity elutes at a KCl concentration of about 150 mM. Fractions containing activity are pooled and the proteins concentrated by ultrafiltration. At this stage, the enzyme is suitable for high capacity screening tests that are designed to discover inhibitory compounds. Alternatively, hydrophobic interaction chromatography can be used instead of DEAE-cellulose. This material is optionally further purified by passage through a column of Sephadex G-75 equilibrated with the chromatography buffer described above. The peak of ADSS activity elutes at a retention volume corresponding to a molecular weight of approximately 50,000 Da. This preparation is largely free both of undesired GTPases and IMP 5'-nucleotidases which compete with the substrates in the assay, and is suitable for detailed kinetic studies.

B. Assay of ADSS:

ADSS is assayed by anion exchange HPLC and by a continuous spectrophotometric assay. For the former, enzyme is diluted appropriately with 50 mM EPPS, pH 8.3, 10% ethylene glycol, 10 mM potassium phosphate and 1 mM $MgCl_2$ to a volume of 92 µL. Reactions are started by addition of an 8 µL aliquot of a mixture of aspartate, IMP and GTP, resulting in final concentrations of 3 mM, 0.4 mM and 0.2 mM, respectively. Reactions are stopped by adding 1 µL of 4N HCl. 95 µL of the reaction mixture is injected to a Hamilton PRP-X100 column equilibrated with 3% acetonitrile. Reactants and products are eluted with a convex gradient (Curve=–2) to 6% 1M potassium phosphate, pH 7, and 12% 2M KCl delivered during a span of 30 min by a Perkin-Elmer 410 BIO pump. The column eluate is monitored at 270 nm using a Perkin-Elmer LC 480 diode array detector. Integrated peaks are quantified from standard curves. Identity of the products of the ADSS reaction, GDP and adenylosuccinate, are determined by comparing their retention times and spectra with those of authentic standards, purchased from Sigma Chemical Co.

For the spectrophotometric assay, reaction mixtures are the same as above, except that the volume is doubled. The addition of IMP starts the reaction and formation of adenylosuccinate (AS) is monitored at 280 nm for 10–15 minutes. The optical density increases as AS is formed. The amount of product formed is calculated from the extinction coefficient of AS (4847 AU/cm/M) and that of IMP (895 AU/cm/M), assuming that one mole of IMP is consumed per mole of AS formed. When testing probe compounds for inhibition of ADSS an initial dose of 100 µM is used. This method of quantification was validated using the HPLC method.

Figure 5:
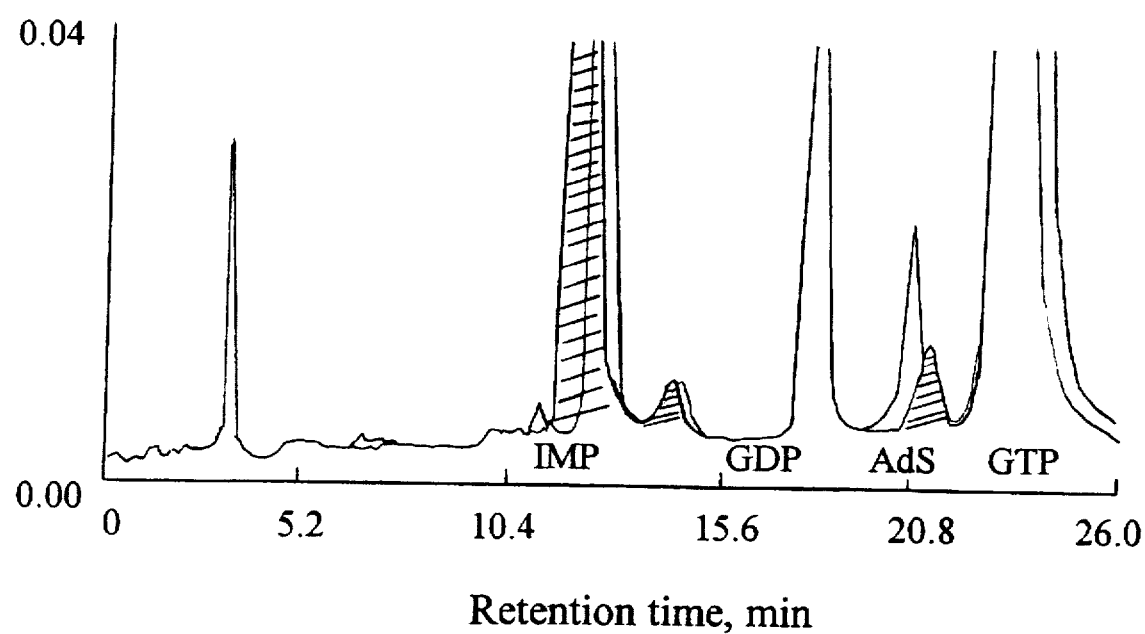
FIG. 5 illustrates inhibition of ADSS from wheat germ by 5'-Phospho-N-acetyl-hydantocidin (NAP-H).
Figure 6A:
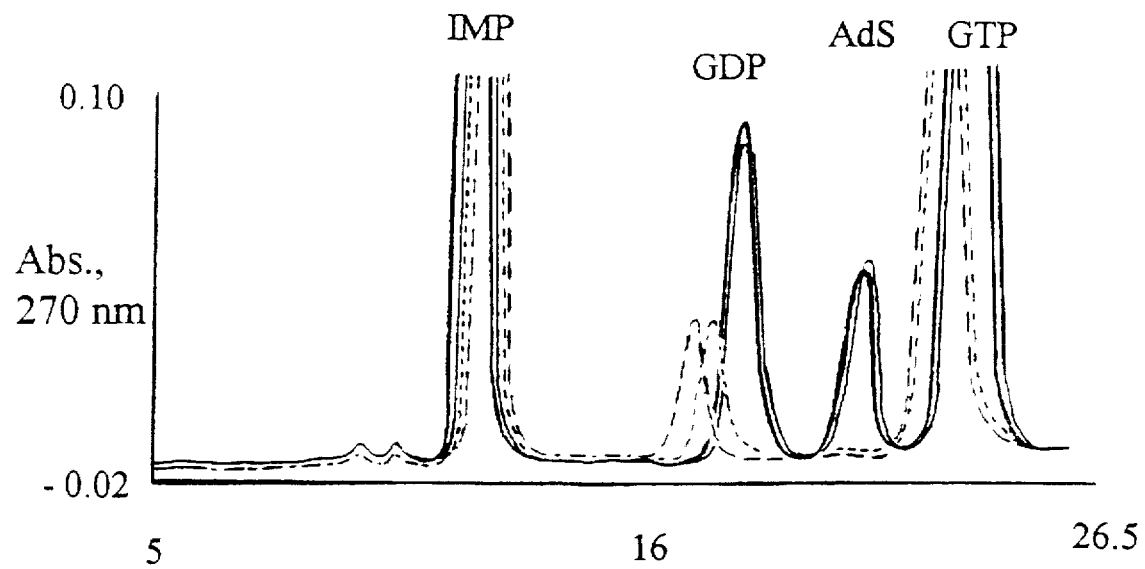
FIG. 6 compares inhibition of ADSS from *E.coli* and rat liver by 5'-Phospho-N-acetyl-hydantocidin (NAP-H) and hadacidin.
Figure 6B:
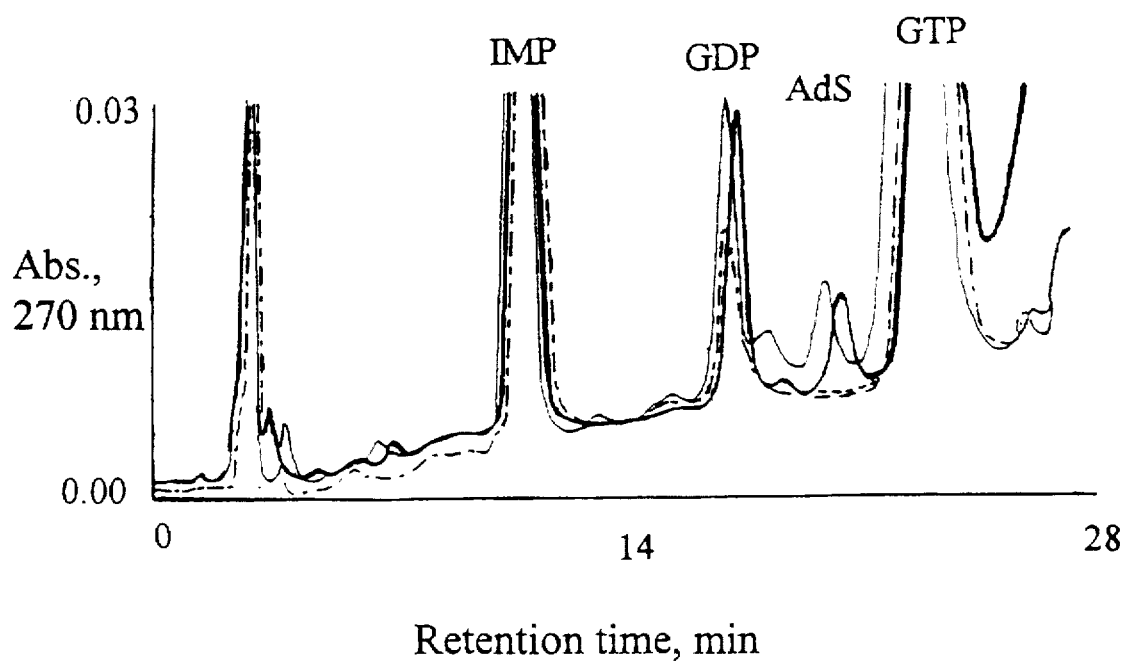

C. Inhibition of ADSS by hydantocidin, N-acetyl hydantocidin, NAP-H and hadacidin:

Inhibition of ADSS by 10 µM NAP-H is initially observed in the crude (desalted) extract from wheat germ using the HPLC assay (FIG. 5). Product is not formed when NAP-H or hadacidin are presented at 100 µM to ADSS isolated from maize (not shown), wheat germ (not shown), *E. coli* (FIG. 6) or rat liver (FIG. 6). FIG. 6 also shows that neither the *E. coli* nor the rat liver ADSS are inhibited by hydantocidin and N-acetyl hydantocidin. This is also true for ADSS isolated from both plant species (not shown). The $I_{50}$ for inhibition of ADSS by hadacidin under these conditions is determined to be $3 \times 10^{-6}$M.

Figure 7:
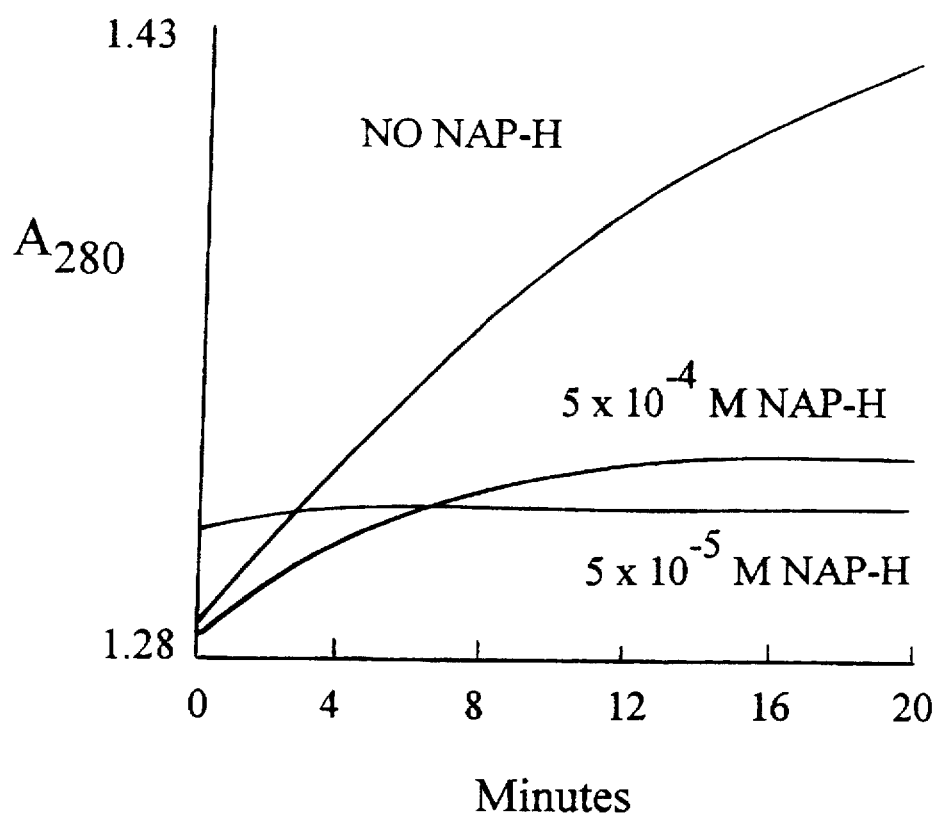
FIG. 7 illustrates the time course of ADSS inhibition in the presence of 5'-Phospho-N-acetyl-hydantocidin (NAP-H).
Figure 8:
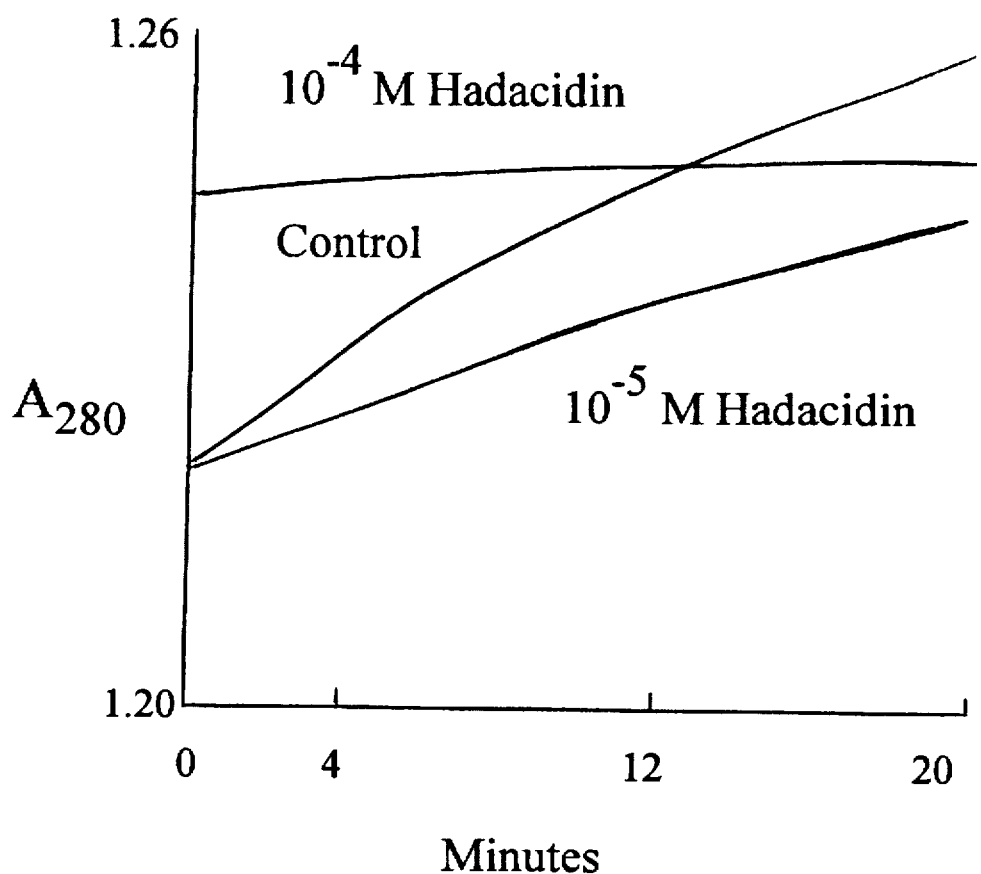
FIG. 8 illustrates the time course of ADSS inhibition in the presence of hadacidin.

Inhibition of ADSS by 5 µM NAP-H is confirmed by the spectrophotometric assay, which monitors product formation continuously. The time course of the ADSS reaction that results when substrates are added to a mixture of enzyme and NAP-H is shown in FIG. 7. Inhibition is initially weak, but becomes greater during a time span that depends on the concentration of NAP-H. The same time course is observed if the enzyme is preincubated with various concentrations of NAP-H for 30 min prior to starting the reaction with the addition of substrates, suggesting that substrate(s) must be present in order for the inhibitor to inactivate the enzyme (not shown). This time-dependent inhibition occurs with inhibitors that either bind very tightly to the enzyme, form a covalent bond with the enzyme, or bind less tightly but in doing so, inactivate the enzyme. The latter two possibilities can be eliminated by showing that inhibition is reversible. To do this, enzyme is incubated with 4 µM NAP-H, with or without the usual mixture of substrates, for 10 min, then passed through a column of Sephadex G-25 to separate enzyme from inhibitor. The enzyme is assayed immediately after traversing the column, which requires approximately 12 min. The reaction rates in the subsequent assay are the same whether inhibitor is present during the preincubation or not (not shown). Thus inhibition is reversible. Dependence of inhibition by NAP-H or incubation time is not a general property of ADSS, as shown from the time course of inhibition by hadacidin (FIG. 8). Hadacidin is known to inhibit ADSS competitively with aspartate. Inhibition by ADSS by hadacidin is not time dependent, but linear within the time it takes to mix the reactants.

These results clearly demonstrate that NAP-H is the actual inhibitor of ADSS. Although no enzyme inhibition is observed with hydantocidin and N-acetylhydantocidin, results with Arabidopsis bioassay clearly suggest that their mode of action is similar to that of NAP-H. Thus, it is hypothesized that both hydantocidin and N-acetylhydantocidin must be phosphorylated in the plant prior to inhibition of ADSS.

D. Preparation of Adenylosuccinate Lyase (ASL):

ASL is obtained from three day old, etiolated seedlings of *Zea mays* (maize). Seedlings are homogenized in a Waring blender with an equal volume (grams of tissue=mls of buffer) of 20 mM potassium phosphate buffer (KP buffer) containing 1 mM DTT. The slurry is then filtered through a cheese cloth and the filtrate subjected to 100,000×g centrifugation for 60 minutes. The clear supernatant is used for assaying ASL activity.

E. Assay of ASL:

A typical reaction mixture in 1 mL contains 100–300 µL of ASL and 0.15 mM adenylosuccinate (30 µL of a 5 mM solution in KP buffer), the rest being KP buffer. Disappearance of absorbance at 280 nm is followed as a function of time to determine the rate of ASL activity. Inhibitors when needed are included to a final concentration of 1 mM in the assay mixture to observe the effect on the ASL activity. Compounds hydantocidin, N-acetylhydantocidin, NAP-H and hadacidin had no effect on the rate of ASL activity at 1 mM concentration (data not shown).

It is clear from the Arabidopsis bioassay and ADSS assay that compounds NAP-H and hadacidin are direct inhibitors of ADSS whereas compounds of hydantocidin and N-acetylhydantocidin have to be phosphorylated in Arabidopsis prior to inhibition of the enzyme.

EXAMPLE 6

Herbicidal Greenhouse Tests

The above described Arabidopsis screening method demonstrates good correlation with herbicidal greenhouse data. In general, the herbicidal greenhouse tests are conducted as follows: A probe compound is weighed and dissolved in a stock solution consisting of acetone or DSMO:deionized water (1:1) and 0.5% adjuvant mixture. Dilutions from this stock solution are performed to allow for preparation of spray solutions consisting of single doses applied at a level equivalent to either 4.0, 1.0 or 0.25 kg/ha of active ingredient. The solutions are applied by a linear track sprayer set to deliver 1000 L/ha spray volume. Both broadleaf and grassy weed species are tested. Herbicidal control is evaluated as % injury with 100% injury considered complete control. The herbicidal effect is determined in both preemergence and post-emergent studies.

In post-emergent studies each dose of compound is applied to the foliage of the selected weed species. The weed plants are allowed to grow in the greenhouse and visually evaluated at 1, 7 and 19 days after treatment.

When a probe compound is screened in the Arabidopsis bioassay herein described and is found to be inactive, the same compound is also found to be inactive in the herbicidal screening studies at 1.0 kg/ha. Inactivity is considered to be on average approximately 10% or less injury. Likewise, a probe compound which is determined to be active in the Arabidopsis assay and wherein reversion of growth inhibition is determined with AMP, the compound is found to cause weed injury in the herbicidal screening tests. The amount of injury varies with each probe compound and with the type of weed species, but in general overall injury when the compound is applied at 1.0 kg/ha is greater than 40% and in some weed species the injury will be greater than 70%.

One skilled in the art is aware of procedures to make various hydantocidin derivatives. These methods are disclose in references such as, DE 4129728, DE 4129616, JP 2167283 and in U.S. patent application Ser. No. 315,796 filed Sep. 30, 1994. These references are hereby incorporated by reference.

What is claimed is:

1. A method for identifying a probe compound that inhibits plant AMP biosynthesis, said method comprising;
    a) exposing plant material capable of expressing the enzyme adenylosuccinate synthetase and adenylosuccinate lyase to a concentration range of a probe compound;
    b) determining a lethal concentration range of said probe compound;
    c) exposing plant material capable of expressing said enzymes to the lethal concentration range of said probe compound and concurrently exposing said material to a concentration range of one or more antidote compounds; and
    d) selecting the probe compound that inhibits growth of the plant material at a lethal concentration range of said probe compound but does not inhibit growth of the plant material when exposed to the antidote compound.

2. The method for identifying a probe compound that inhibits plant AMP biosynthesis according to claim 1 wherein said method comprises a two-step procedure,
    a) the first step includes the determination of a lethal concentration which comprises:
        1) maintaining plant material capable of expressing the enzyme adenylosuccinate synthetase and adenylosuccinate lyase under test conditions suitable for growth of the plant material;
        2) contacting a probe compound at a concentration range of about 0.01 ppm to about 500 ppm with the plant material of 1);
        3) allowing the probe compound and plant material to incubate; and
        4) measuring the inhibition of growth of the plant material and determining the lethal concentration of the probe compound;
    b) the second step includes the determination of reversal conditions which comprises:
        5) maintaining plant material as stated in step 1);
        6) contacting the plant material with the probe compound and one or more antidote compounds wherein the concentration of the probe compound is at the lethal concentration and the concentration of the antidote compounds are in the range of about 0.001 to about 5.0 mM;
        7) allowing the plant material to grow in the presence of the probe compound and antidote compound;
        8) measuring the growth of the plant material and
    selecting the probe compound that inhibits growth of the plant material under step a) but does not inhibit growth of the plant material under reversal conditions of step b).

3. The method according to claim 1 wherein the plant material is Arabidopsis seed.

4. The method according to claim 1 wherein the antidote compound is at least one of the compounds slected from the group consisitng of adenosine, ADP, AMP and adenine.

5. An inhibitor of AMP biosynthesis identified according to the method in claim 1.

6. The inhibitor according to claim 5 wherein said inhibitor is a phosphorylated compound.

7. The inhibitor according to claim 5 wherein said inhibitor is a non-phosphorylated compound.

8. The method according to claim 2,
 a) wherein the first step includes the determination of a lethal concentration which comprises:
  1) adding a concentration range of about 0.01 to 500 ppm of a probe compound to wells of a support;
  2) dispensing media capable of sustaining seed growth in said wells;
  3) adding plant seeds capable of expressing the enzyme adenylosuccinate synthetase and adenylosuccinate lyase to said wells;
  4) allowing the probe compound and the seeds to incubate under test conditions suitable for growth of said seed;
  5) measuring the inhibition growth of the seeds; and
  6) determining the lethal concentration of the probe compound; and
 b) wherein the second step includes the determination of reversal conditions which comprises:
  7) adding about the lethal concentration of the probe compound to wells in a support;
  8) adding one or more antidote compounds separately to said wells;
  9) dispensing media capable of sustaining growth in said wells;
  10) adding plant seeds capable of expressing said enzymes to the wells;
  11) allowing the seeds to germinate in the presence of the probe compound and antidote compound;
  12) measuring the growth of said seeds as compared to a control wherein the control lacks the antidote compounds of step 8) and
 identifying a compound that inhibits growth of the seeds under the lethal concentration but does not inhibit growth of said seeds under reversal conditions.

9. An herbicidal composition comprising as an active ingredient a herbicidally effective amount of a probe compound selected according to claim 1.

10. A method of controlling undesired plant growth by applying to a locus where control is desired a herbicidal composition according to claim 9.

11. A method for screening and selecting a compound that inhibits an enzyme in the plant purine ribonucleotide biosynthetic pathway selected from the group consisting of PRPP kinase, amidophosphoribosyl transferase, GAR synthetase, GAR transformylase, FGAM synthetase, AIR synthetase, AIR carboxylase, SACAIR synthetase, adenylosuccinate lyase, AICAR transformylase, IMP cyclohydrolase, IMP dehydrogenase, GMP synthase, adenylosuccinate synthetase and adenylosuccinate lyase, said method comprising a two-step procedure:
 a) wherein the first step includes the determination of a lethal concentration which comprises:
  1) maintaining plant material capable of expressing said enzyme under test conditions suitable for growth of the plant material;
  2) contacting a probe compound at a concentration range of about 0.01 ppm to about 500 ppm with the plant material of 1);
  3) allowing the probe compound and plant material to incubate; and
  4) measuring the growth of the plant material and determining the lethal concentration of the probe compound;
 b) wherein the second step includes the determination of reversal conditions which comprises:
  5) maintaining plant material as stated in step 1);
  6) contacting the plant material with the probe compound and one or more antidote compounds wherein the concentration of the probe compound is at the lethal concentration and the concentration of the antidote compounds are in the range of about 0.001 to about 5.0 mM;
  7) allowing the plant material to grow in the presence of the probe compound and antidote compound;
  8) measuring the growth of the plant material and
  selecting the probe compound that inhibits growth of the plant material under test conditions but does not inhibit growth of the plant material under reversal conditions.

12. An inhibitor selected according to the method in claim 11.

13. An in vitro enzyme assay for determining the mode of action of a probe compound comprising;
 a) obtaining substantially pure adenylosuccinate synthase;
 b) mixing the probe compound with adenylosuccinate synthase, guanosine triphosphate and aspartate;
 c) allowing pre-incubation of the reaction mixture;
 d) adding substrate inosine monophosphate and allowing the substrate and reaction mixture to react;
 e) monitoring the formation of adenylosuccinate as influenced by the probe compound; and
 f) comparing the amount of adenylosuccinate produced in the presence of the probe compound with that produced with the absence of a probe compound.

14. A method for screening novel compounds as inhibitors of adenylosuccinate synthase comprising the use of the in vitro enzyme assay of claim 13.

15. An inhibitor screened according the method of claim 14.

16. A method of controlling undesired plant growth by applying to a locus where control is desired a herbicidally effective amount of an inhibitory compound identified according to claim 14.

17. The method according to claim 14 wherein said inhibitory compound is a non-phosphorylated compound.

18. The method according to claim 14 wherein said inhibitory compound is a phosphorylated compound.

19. A method of activating the adenylosuccinate synthase inhibitory effect of a compound wherein said compound inhibits adenylosuccinate synthase by the same mode of action as NAP-H comprising applying to a plant or a locus where control is desired an adenylosuccinate synthase inhibitory compound which is phosphorylated prior to contacting adenylosuccinate synthase.

20. A method of inactivating the adenylosuccinate synthase inhibitory effect of a herbicidal phosphorylated adenylosuccinate synthase inhibitor comprising applying to a plant or locus where control is desired a phosphorylated adenylosuccinate synthase inhibitory compound which is dephosphorylated prior to contacting adenylosuccinate synthase.

21. The assay according to claim 13 wherein, (a) the concentration range of adenylosuccinate synthase in the assay is sufficient to generate about 10 μM to about 50 μM of adenylosuccinate in 60 minutes; (b) the concentration range of the probe compound is about 0.5 μM to about 150 μM; (c) the concentration range of guanosine triphosphate is about 70 μM to about 200 μM; (d) the concentration range of aspartate is about 3 μM to about 10 μM; and (e) the concentration range of inosine monophosphate is about 100 μM to about 400 μM.

22. An in vitro enzyme assay for determining the mode of action of a probe compound comprising a) obtaining substantially pure adenylosuccinate synthase;

b) mixing the probe compound with adenyloduccinate synthase, guanosine triphosphate and aspartate;

c) allowing pre-incubation of the reaction mixture;

d) adding substrate inosine monophosphate and allowing the substrate and reaction mixture to react and;

e) measuring the formation of product adenylosuccinate.

23. A method for screening novel compounds as inhibitors of adenylosuccinate synthase comprising the use of the enzyme assay of claim 22.

* * * * *